(12) United States Patent
Allen

(10) Patent No.: US 12,740,845 B2
(45) Date of Patent: Sep. 22, 2026

(54) OPHTHALMIC VIEWING DEVICES

(71) Applicant: Alcon Inc., Fribourg (CH)

(72) Inventor: Douglas Allen, Santa Barbara, CA (US)

(73) Assignee: Alcon Inc., Fribourg (CH)

( * ) Notice: Subject to any disclaimer, the term of this patent is extended or adjusted under 35 U.S.C. 154(b) by 406 days.

(21) Appl. No.: 18/362,490

(22) Filed: Jul. 31, 2023

(65) Prior Publication Data

US 2024/0041555 A1 Feb. 8, 2024

Related U.S. Application Data

(60) Provisional application No. 63/394,877, filed on Aug. 3, 2022.

(51) Int. Cl.
*A61B 90/25* (2016.01)
*A61F 9/007* (2006.01)

(52) U.S. Cl.
CPC .............. *A61B 90/25* (2016.02); *A61F 9/007* (2013.01)

(58) Field of Classification Search
CPC .. A61B 90/25; A61B 3/13; A61B 3/14; A61B 3/12; A61F 9/007; G02B 21/0012; G02B 21/06
See application file for complete search history.

(56) References Cited

U.S. PATENT DOCUMENTS 4,932,774 A 6/1990 Takagi
2004/0183999 A1 9/2004 Kogawa
2005/0280891 A1* 12/2005 Bogle .................. G02B 21/361 359/368
2008/0043199 A1 2/2008 Whalen
2008/0204660 A1* 8/2008 Obrebski ................. A61B 3/14 351/221
2013/0103145 A1* 4/2013 John ..................... A61F 9/0017 351/219
2015/0313465 A1* 11/2015 Graham ................. A61B 3/117 351/219
2020/0093545 A1* 3/2020 Sakaguchi ............. A61B 1/247
2021/0315455 A1* 10/2021 Delong .................... A61B 3/14
2023/0371810 A1* 11/2023 Annen .................... A61F 9/009

FOREIGN PATENT DOCUMENTS

CN 1523393 A 8/2004
EP 3310309 B1 8/2021

* cited by examiner

*Primary Examiner* — William R Alexander
*Assistant Examiner* — Mackenzi Bourquine

(57) ABSTRACT

An ophthalmic viewing device is provided. The ophthalmic viewing device includes a mounting feature, an upper arm, a lower arm, a first movable mirror, a second mirror, and a lens assembly having a lens frame. When the ophthalmic viewing device is in a first configuration, the movable mirror and the lens frame are outside an on-axis optical path between a visualization device and an eye being visualized. When the ophthalmic viewing device is in a second configuration, the first mirror, the second mirror, and the lens frame are configured to redirect the optical path between the patient's eye and the visualization device to an off-axis optical path that is angled from the eye relative to the on-axis optical path.

17 Claims, 5 Drawing Sheets

OPHTHALMIC VIEWING DEVICES

BACKGROUND

During various ophthalmic surgeries microscopes, often digital microscopes, are used to provide the surgeon with a magnified, high-quality image of optical components of the eye. For example, during vitreoretinal surgeries, surgeons view the eye anatomy through a digital microscope that captures light reflected directly from the eye. Once the surgical objective is achieved, an important step of many surgeries is to verify that the tissues on the circumference of the eye are intact. However, the tissues on the circumference of the eye are outside the field of vision of traditional microscopes used for viewing the back of the eye.

As an example, upon the completion of a vitreoretinal surgery, it is necessary to view the ora *serrata*, the terminus of the retina situated approximately 5 millimeters anterior to the equator of the eye, as surgeons often find post-surgical tears or puckers in the ora *serrata* region of the retina as a result of the vitreoretinal surgery. If a tear or pucker is not recognized and fixed as part of the vitreoretinal surgery, the patient will require another surgery to repair the retina.

However, as discussed, the ora *serrata* is often outside the field of vision of the microscope. To bring the ora *serrata* into view and check for tears or puckers, surgeons will often manipulate the eye using pushing or twisting, either manually or with a tool. Not only can this can be tedious, difficult, or potentially harmful to the eye, but it can also cause the visual axis of the eye to no longer be aligned with the optical axis of the microscope. Thus, there exists a need in the art for an improved viewing device that allows microscopic viewing of a field of vision including the ora *serrata* that keeps the visual axis of the eye and the microscope aligned, without requiring or lessening the need for adjustment or manipulation of the eye.

SUMMARY

The present disclosure relates generally to ophthalmic viewing devices and to systems and method of using such viewing devices.

Certain embodiments disclosed herein provide ophthalmic viewing devices ("viewing devices") suitable for being removably mounted to ophthalmic visualization devices, such as microscopes. In certain embodiments, an ophthalmic viewing device may comprise: a mounting feature configured for mounting the viewing device to a visualization device, an upper arm connected to the mounting feature proximate a proximate end of the upper arm, and a lower arm connected to the upper arm proximate a distal end of the upper arm. The ophthalmic viewing device may further comprise a first mirror movably connected to the mounting feature and having at least a first mirror position and a second mirror position, a second mirror connected to the upper arm, and a lens assembly having a lens frame configured to shift between a first lens frame position and a second lens frame position. The lens frame may have a central cavity configured for receiving a lens.

The ophthalmic viewing device may have a first configuration and a second configuration. In the first configuration of the ophthalmic viewing device, the lens frame is in the first lens frame position. In the first lens frame position, a plane of the central cavity is perpendicular to an axis of the visualization device ("visualization device axis") along an on-axis optical path between a patient's eye and the visualization device, and the first mirror is in the first mirror position outside of the on-axis optical path.

In a second configuration of the ophthalmic viewing device, the lens frame is in the second lens frame position. In the second lens frame position, the plane of the central cavity is disposed at a frame angle relative to the visualization device axis, such that the plane of the central cavity is perpendicular to a first angled axis of an off-axis optical path. Also in the second configuration of the ophthalmic viewing device, the first mirror is in the second mirror position. When in the second mirror position, the first mirror at least partially intercepts the on-axis optical path, and is positioned at a first angle relative to the visualization device axis for redirecting the off-axis optical path, received along a second angled axis from the second mirror, towards the visualization device. In the second configuration of the ophthalmic viewing device, the second mirror is positioned within the off-axis optical path at a second angle relative to the visualization device axis, and the second mirror is configured to redirect the off-axis optical path, received along the first angled axis from the lens in the lens frame in the second lens frame position, towards the first mirror.

The following description and the related drawings set forth in detail certain illustrative features of one or more embodiments.

BRIEF DESCRIPTION OF THE DRAWINGS

The drawings described herein are for illustrative purposes only, are schematic in nature, and are intended to be exemplary rather than to limit the scope of the disclosure.

The above summary is not intended to represent every possible embodiment or every aspect of the subject disclosure. Rather, the foregoing summary is intended to exemplify some of the novel aspects and features disclosed herein. The above features and advantages, and other features and advantages of the subject disclosure, will be readily apparent from the following detailed description of representative embodiments and modes for carrying out the subject disclosure when taken in connection with the accompanying drawings and the appended claims.

DETAILED DESCRIPTION

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that the reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Note that, as described herein, a distal end or portion of a component refers to the end or portion that is closer to the patient during use. Alternatively, a proximal end or portion of the component refers to the end or portion that is distanced further away from the patient. Thus, a distal end or portion may be a bottom portion, end, or side, and a proximal end or portion may be a top portion, end, or side, when a viewing device (e.g., viewing device 102 of FIG. 1) is oriented above a patient to look down into the patient's eye.

Figure 1:
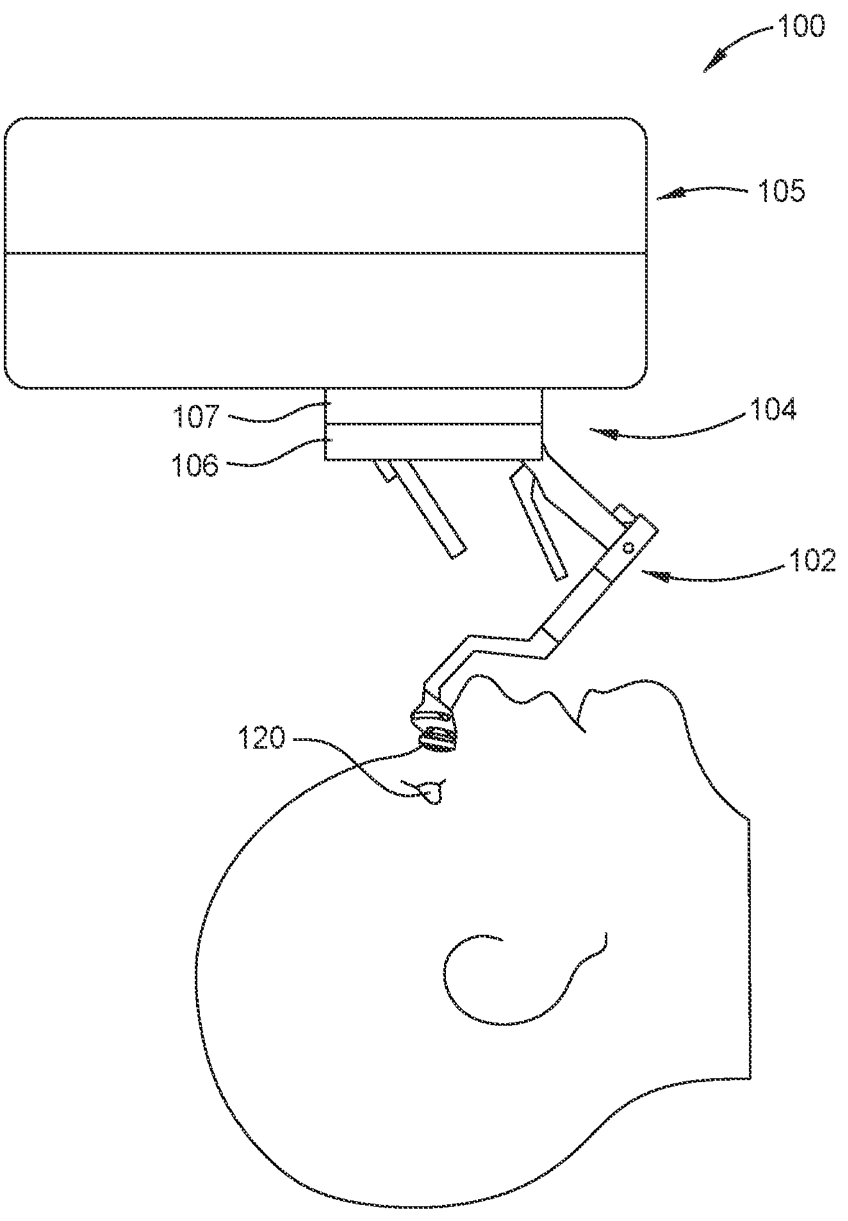
FIG. 1 shows a schematic diagram of an exemplary ophthalmic visualization system including an ophthalmic viewing device, according to certain embodiments.

FIG. 1 shows a schematic diagram of an exemplary ophthalmic visualization system 100 including an ophthalmic viewing device 102 ("viewing device 102") and a visualization device 105. In the embodiments described herein, the visualization device 105 is a microscope, such as a digital microscope. However, a visualization device 105 other than a microscope could also be used in accordance with features of the present invention without departing from the scope of this disclosure. The viewing device 102 is removably attached to the visualization device 105 or another visualization device. In some embodiments, it may be preferable that the viewing device 102 be permanently mounted to the visualization device 105. The visualization device 105 includes optical components allowing a surgeon to visualize the patient's eye 120 and components of the eye 120 in more detail to accomplish surgical objectives. One example visualization device 105 suitable for this purpose is the ALCON LuxOR® Revalia™ ophthalmic microscope.

During vitreoretinal surgery, a surgeon may currently position a visualization device 105 above the patient such that the optical axis of the visualization device is perpendicular to the patient (e.g., perpendicular to the surgical bed the patient is position on) and aligned with the patient's eye. Such an arrangement is effective for the surgeon to view the back of the eye during the procedure, but does not allow for flexibility in viewing the equator of the eye and the upper wall of the eye.

Figure 2A:
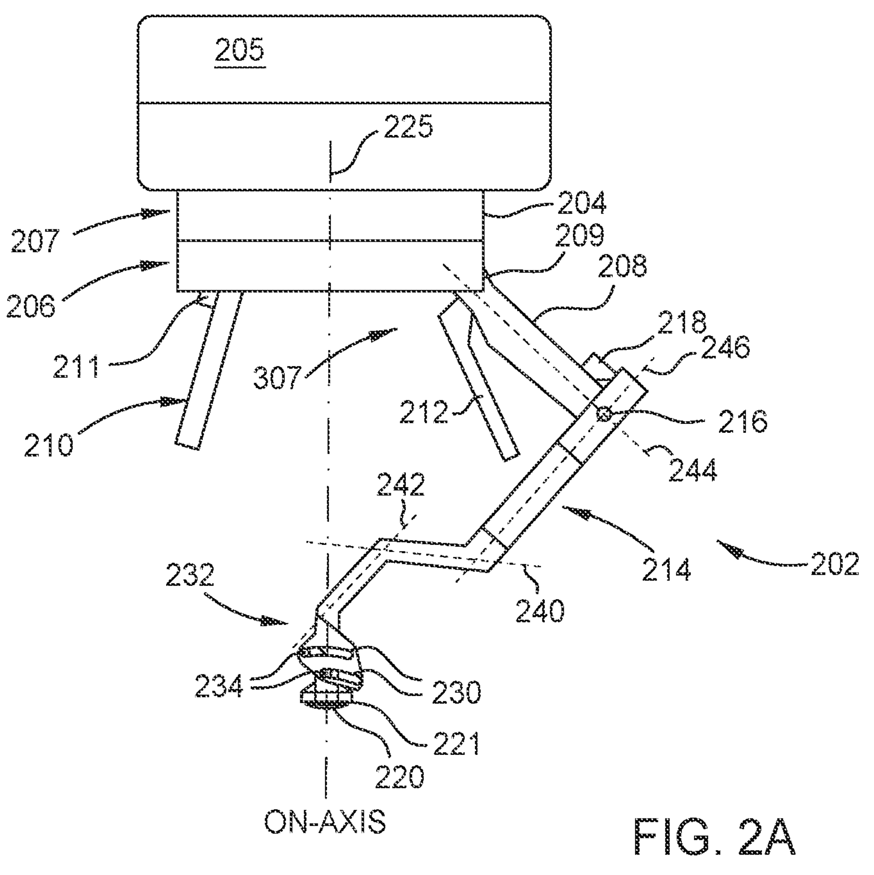
FIG. 2A shows an ophthalmic viewing device in a first configuration, according to certain embodiments.
Figure 2B:
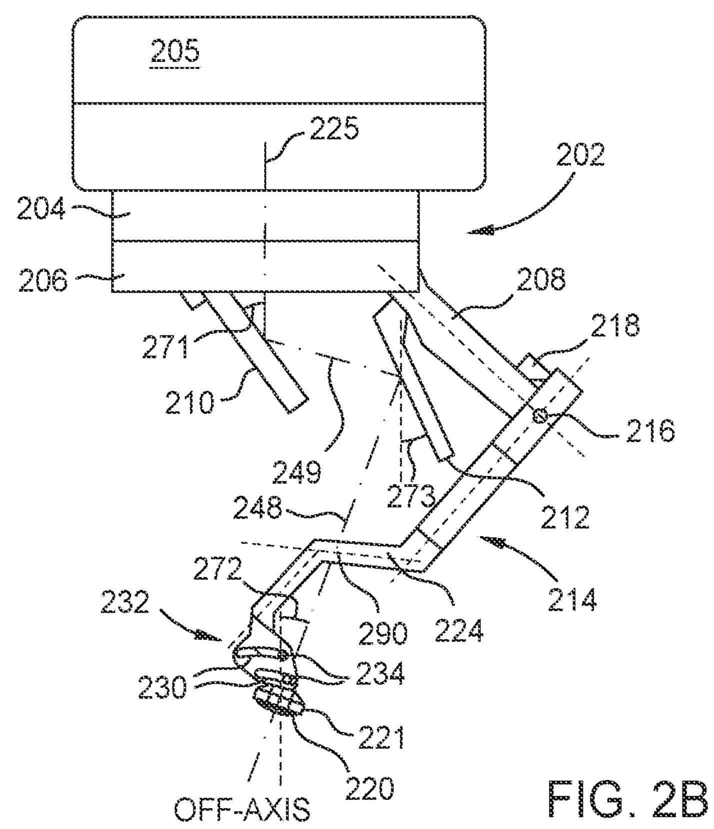
FIG. 2B shows an ophthalmic viewing device in a second configuration, according to certain embodiments.

Accordingly, to conveniently view the equator and upper wall of the eye 120, the viewing device 102 can have at least two configurations, including a first, on-axis configuration for viewing the back of the eye during the procedure, and a second, off-axis configuration, as shown by, for example, FIGS. 1 and 2B, for viewing the equatorial and upper wall portions of the eye 120 with little or no manual manipulation of the eye 120. In this way, the combined field of view of the viewing device 102 is widened compared to the field of view of a conventional viewing device.

As shown by FIG. 1, the viewing device 102 is mounted to a visualization device 105 positioned, for example, above a patient's eye during surgery. The viewing device 102 includes a mounting feature 104. The mounting feature 104 includes a stationary mounting ring 107 that is used to mount the viewing device 102 to the visualization device 105. The stationary mounting ring 107 is movably coupled to a rotatable ring 106, allowing for the rotatable ring 106, and thereby the viewing device 102, to be rotated in a 360 degree rotation with respect to the stationary mounting ring 107. In some embodiments, a remote or foot-activated pedal may be used to control the rotation.

FIG. 2A shows an ophthalmic viewing device 202 in a first, on-axis configuration, according to certain embodiments. As shown, when in the first configuration, the viewing device 202 allows for viewing a patient's eye along the visualization device axis 225.

In the shown embodiment, an upper arm 208 is attached to the rotatable ring 206 at a first attachment location 209. A top end of a movable mirror 210 is pivotably attached to the rotatable ring 206 at a second attachment location 211. A lower arm 214 is moveably or removably attached to the upper arm 208. The lower arm 214 has two parallel and similarly shaped extensions (shown in FIG. 3B).

As shown in FIG. 2A, the movable mirror 210 is in a first configuration corresponding to the viewing device 202 being in the on-axis position or configuration. When the viewing device 202 is in the on-axis configuration, an optical path extending along the visualization device axis 225 is unobstructed between the visualization device and a lens 220 located on a lower arm 214. In particular, the moving mirror 210 and a fixed mirror 212 are positioned outside the optical path. In this configuration, the visualization device axis 225 is perpendicular to the plane of a lens 220 (or the plane of a lens frame or mounting 221 in which the lens 220 is mounted).

In some embodiments, the upper arm 208 has an axis 244 which creates an angle, between 90 and 180 degrees relative to axis 225. The upper arm 208 is hingably attached to the lower arm 214 with an attachment pin 216 to create a hinged connection-location. The upper part of the lower arm 214 has an axis 246 which creates a second angle, between 0 and 90 degrees relative to the axis 225. The middle part of the lower arm 214 has an axis 240 which creates a third angle, between 45 and 135 degrees relative to the axis 225, and the lower part of the lower arm 214 comprises a second axis 242 which creates a fourth angle, between 0 and 90 degrees relative to the axis 225.

The axis 240 and axis 242 of the lower arm 214 correspond to a shape of the lower arm 214 that can assist in avoiding potential obstacles in the path of the lower arm 214 as the viewing device 102 rotates in a 360 degree path around the axis 225. According to various embodiments, one or more of the first angle, the second angle, the third angle may be selected such that the viewing device 102 is able to rotate freely without being obstructed by, for example, a nose or brow of a patient, while positioning the lens 220 along the optical path of a visualization device suitable for examining or operating on a patient's eye.

According to some embodiments, the lower arm 214 is prevented from excess motion in one direction by a stop feature 218 attached to the upper arm 208. When no upward pressure is present on the lower arm 214, the proximal or upper end of the lower arm 214 rests against the stop feature 218. The stop feature 218 is sized and positioned on the upper arm 208 such that, when the proximal end of the lower arm 214 rests against the stop feature 218, the lens 220 can be positioned at a standard distance from the visualization device 105. The lower arm 214 is restricted from excess motion in the direction of the patient, preventing collision between the viewing device 102 and the patient, but may move freely in the opposite direction. Upward force applied to lower arm 214 will cause it to fold towards the rotatable ring 206 and away from the patient.

Therefore, the arrangement of the upper arm 208, stop feature 218, and the lower arm 214 provides a safety function, such that when force is applied to the lower arm 214 as a result of the lower arm 214 encountering an obstacle during the rotation of the viewing device 102, the lower arm 214 will fold up, away from the patient. An obstacle may, for example, be the patient's nose, a surgical instrument used for the surgical procedure, etc.

In some embodiments, a pair of slots 230 are provided at the distal end of each of the extensions of the lower arm 214. A rotatable lens assembly 232 is configured to interact with the pairs of slots 230 provided at the distal ends of the extensions of the lower arm 214. The lens assembly 232 comprises a lens frame 221 for holding the lens 220 positioned in a central cavity of the lens frame 221. The lens assembly 232 further includes a pair of pins 234 on each side, configured to slide between a first end and a second end of the pair of slots 230 respectively located on each side of the lens assembly 232. The pair of slots 230 and pins 234 can be configured on each side with an over-center spring mechanism which allows the lens 220 and frame 221 to transition between a first position and a second position. When the lens 220 and frame 221 transition between the first position and the second position, a frame angle of the lens frame 221 changes such that, when in the first position, the lens 220 is perpendicular to the visualization device axis 225, and, when in the second position, the lens 220 is perpendicular to a first angled axis 248, the first angled axis 248 being angled relative to the visualization device axis 225.

In some embodiments, the difference between the first position and the second position may comprise a rotation of between 10 degrees and 30 degrees. In some embodiments, the difference between the first position and the second position may comprise a rotation of between 15 degrees and 25 degrees. In some embodiments, the difference between the first position and the second position may comprise a rotation of between 19 degrees and 21 degrees. In some embodiments, the difference between the first position and the second position may comprise a rotation of about 20 degrees. In some embodiments, the difference between the first position and the second position may comprise a rotation amount chosen to facilitate viewing the back of the eye with the first position and a periphery of the eye with the second position based on, for example, the lengths, relative angles, shapes, or dimensions, of an average patient, an average patient's eye, the upper arm, the lower arm, etc.

It will be appreciated that the over-center spring mechanism, slots 230, and pins 234 could be otherwise configured or omitted, and that the viewing device 202 can have various mechanisms for rotating and shifting the lens 220 from the on-axis position to the off-axis position. For example, the mechanism can be a manual movement, a master lever or switch that repositions both the lens 220 and the movable mirror 210, or an actuator coupled to a button, remote, or foot pedal for repositioning both the lens 220 and the movable mirror 210. In certain embodiments, a single or primary switch located on the viewing device 202, or on a remote, is configured to cause the viewing device 202 to transition between the first configuration and the second configuration.

According to various embodiments, the lens 220 may be any lens suitable for viewing a patient's eye. For example, the lens may be a wide-angle (aspheric) lens, which allows for a relatively larger field of view, capturing a view of the patient's eye that would not be possible with other lens types. As another example, a relatively smaller sized lens 220 may facilitate rotation or positioning of the viewing device 202 to obtain a wider field of view without colliding with the patient or another obstruction, and may be particularly suitable for child or infant patients.

The viewing device 202 may have a disposable lower arm 214 and distal lens 220. Following surgery, a surgeon can remove the pin 216 to release the lower arm 214 and distal lens 220 for disposal. The upper arm 208, the movable mirror 210, and the stationary mirror 212 can be sterilized for subsequent uses in surgery, for example, under high heat and pressure using an autoclave. Accordingly, the upper arm 208, the movable mirror 210, and the stationary mirror 212 may be manufactured from materials suitable for withstanding high heat and temperature.

In the embodiment of FIG. 2A, the viewing device 202 is shown in the on-axis position. The on-axis configuration facilitates seeing the back of the retina in the patient's eye. In this position, the movable mirror 210 does not impede the optical path between the patient's eye and the distal lens 220 extending along the visualization device axis 225. Although the visualization device axis 225 is substantially vertical in the shown embodiment, this is exemplary in nature and need not be the case. Rather, any orientation of visualization device axis 225 may be chosen to be suitable for various purposes as will be understood by a person of ordinary skill in the art.

FIG. 2B shows an exemplary viewing device 202 in the off-axis position, according to certain embodiments. The viewing device 202 includes a mounting feature 204 through which the viewing device 202 is configured to be mounted to visualization device 205. The viewing device 202 includes the components as discussed in FIG. 2A.

Following completion of surgery, it is desirable that surgeons confirm the ora *serrata*, the terminus of the retina in the anterior portion of the eye, is intact. If the ora *serrata* is not intact and the surgeon does not repair any tears or puckers, another surgery will be required. Visualizing the ora *serrata* requires capturing light reflected from the patient's eye at an angle, such as the angle shown in FIG. 2B. In order to allow the visualization device to provide visualization of the ora *serrata*, the viewing device 202 utilizes the mirrors 210, 212 in the off-axis position to redirect the optical path of the visualization device to the eye from a wider angle, allowing visualization of the light reflecting off the terminus of the retina in the anterior portion of the patient's eye 120. Thus the optical path is redirected to provide a field of vision from a wider angle which facilitates viewing the terminus without requiring manual manipulation such as pushing or twisting.

As shown in FIG. 2B, the lens frame 221 and lens 220 are positioned along a first angled axis 248 when the viewing device 102 is in the off-axis configuration. In this configuration, a redirected optical path from the patient's eye through the lens frame 221 and lens 220 follows along the first angled axis 248, which is at least partially intersected by the fixed mirror 212. The fixed mirror 212 redirects the optical path from the patient's eye to follow along a second angled axis 249 towards the movable mirror 210, the second angled axis 249 being angled relative to the visualization device axis 225 and the first angle axis 248. The second angled axis 249 is at least partially intersected by the movable mirror 210, such that the redirected optical path from the patient's eye follows along the visualization device axis 225 and into the visualization device.

In the embodiment of FIG. 2B, the viewing device 202 is shown in the off-axis position, in which the position of the movable mirror 210 is at an angle 271 between 15 and 75 degrees relative to the visualization device axis 225. However, the angle could be chosen to be greater or smaller if suitable for a particular application, as would be understood by a person of ordinary skill in the art.

The movable mirror 210 interacts with the light reflecting from the patient's eye 120. The light from the patient's eye is visualized through the distal lens 220, which is positioned at an angle 272 between 15-45 degrees relative to the visualization device axis 225. The angle 272 of the distal lens 220 allows visualization of the light reflecting off the terminus of the retina in the anterior portion of the patient's eye. After the light passes through the distal lens 220, the light is directed to the stationary mirror 212 and finally to the movable mirror 210, which is positioned at an angle 271 between 15 and 45 degrees relative to the visualization device axis 225. The light then reaches the visualization device 205 where the surgeon can visualize the terminus of the retina in the anterior portion of the patient's eye without manual manipulation of the eye. According to various embodiments, the mirrors 210, 212 are angled using angle values chosen based on the size, shape, and dimensions of the upper arm 208, lower arm 214, relative distance between the movable mirror 210, the stationary mirror 212, the visualization device 205, the lens 220, the patient's eye, etc., wherein the angles 271, 272, 273 described herein are measured in relation to the visualization device axis 225.

In some embodiments, the lens 220 may be positioned at 15-25 degrees relative to the axis 225 while the viewing device 202 is in the off-axis position. The stationary mirror 212 is positioned at a fixed angle 273 between 15 and 45 degrees, the angle 273 being selected to redirect an optical path between the distal lens 220 and the movable mirror 210. Redirecting the optical path in such a manner allows the light reflecting back from the patient's eye to be directed to the movable mirror 210 and back to the visualization device 205, enabling visualization of a widened field of vision.

As discussed in reference to FIG. 2B, the viewing device 202 can include a master lever or switch coupled to the movable mirror 210 and the distal lens 220. By using the master lever or switch a user can adjust the angle of mirror 210 and the lens frame 221 simultaneously to shift the movable mirror 210 and the distal lens 220 to the off-axis positions. Alternatively, the viewing device 202 can be coupled to an actuator or other means to allow for autonomous movement from the on-axis position to the off-axis position. In some embodiments, the movable mirror 210 and the distal lens 220 may have more than two positions, such as an on-axis configuration, and multiple off-axis configurations.

Figure 3A:
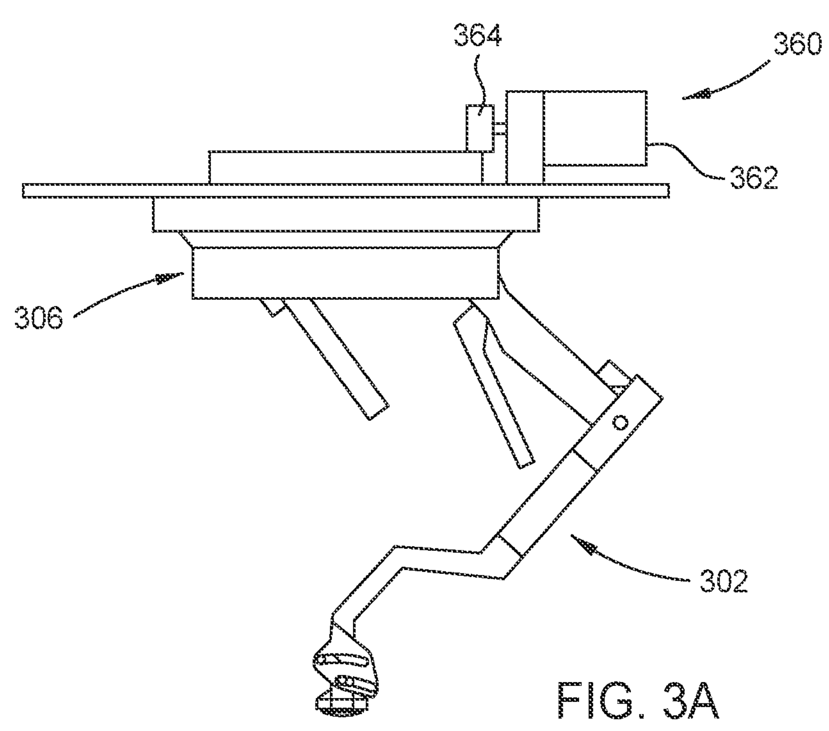
FIG. 3A shows an ophthalmic viewing device having a motorized rotation feature, according to certain embodiments.

FIG. 3A shows an ophthalmic viewing device 302 having a motorized assembly or rotation feature 360, in a profile view, according to certain embodiments. As shown, the rotation feature 360 includes a motor 362 that powers rotation of a spinner 364. In various embodiments, the spinner 364 is a rubber spinner 364 that provides friction sufficient for rotating the viewing device 302, such as by engaging rotatable ring 306, but not sufficient for substantially inhibiting manual rotation so as to cause difficulty when attempting rotation by hand. In various embodiments, the motor 362 may be operated by a switch, remote, or foot-activated pedal.

Figure 3B:
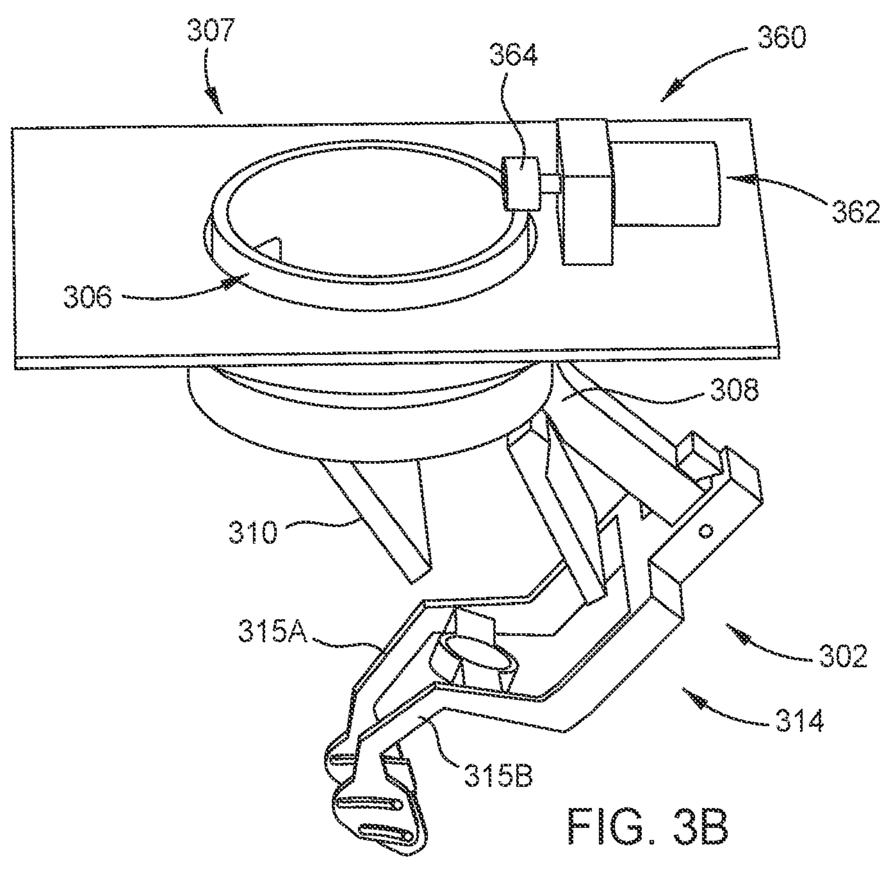
FIG. 3B shows an ophthalmic viewing device having a motorized rotation feature and second lens frame, according to certain embodiments.

FIG. 3B shows the ophthalmic viewing device 302 having the motorized rotation feature 360, in a perspective view, according to certain embodiments. As shown, a movable mirror 310, and an upper arm 308 are attached to the rotatable ring 306, such that their respective arrangement remains unchanged as the ring 306 is rotated with respect to a mounting piece 307. FIG. 3B also illustrates a lower arm 314 with two parallel extensions 315A-B.

Figure 4:
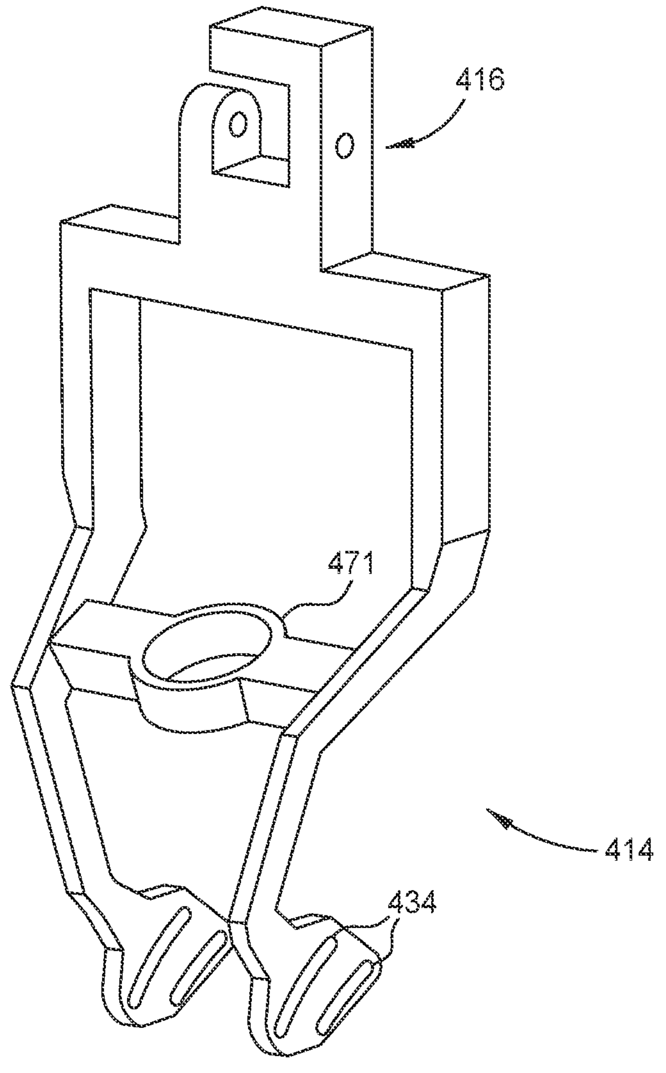
FIG. 4 shows bottom arm of an ophthalmic viewing device, according to certain embodiments.

FIG. 4 shows bottom arm 414 of an ophthalmic viewing device, according to certain embodiments. The bottom arm 414 is similar to the bottom arm 214 with at least the following differences. The bottom arm 414 includes a second, proximal lens frame 471 in which a second, proximal lens may be received. The bottom arm 414 includes a pin and hinge system 416 similar to that shown FIGS. 2A-B. The bottom arm 414 includes two pairs of slots 434 to interact with a lens assembly including a distal lens frame and a distal lens (not shown in FIG. 4), similar to the lens assembly 232 of FIGS. 2A-B. In the embodiments of FIG. 4, the proximal and distal lenses may cooperate to improve or increase the field of vision of a visualization device. Additionally, the lens housed in the lens frame 471 may be located on the lower arm 414 in a position where it is along a first angled axis (e.g., the first angled axis 248 of FIG. 2B), or such as by being integrated in a lower arm similar to lower arm 214 at a location such as location 290 where the first angled axis 248 intersects a first section 224 of the lower arm 214.

Figure 5:
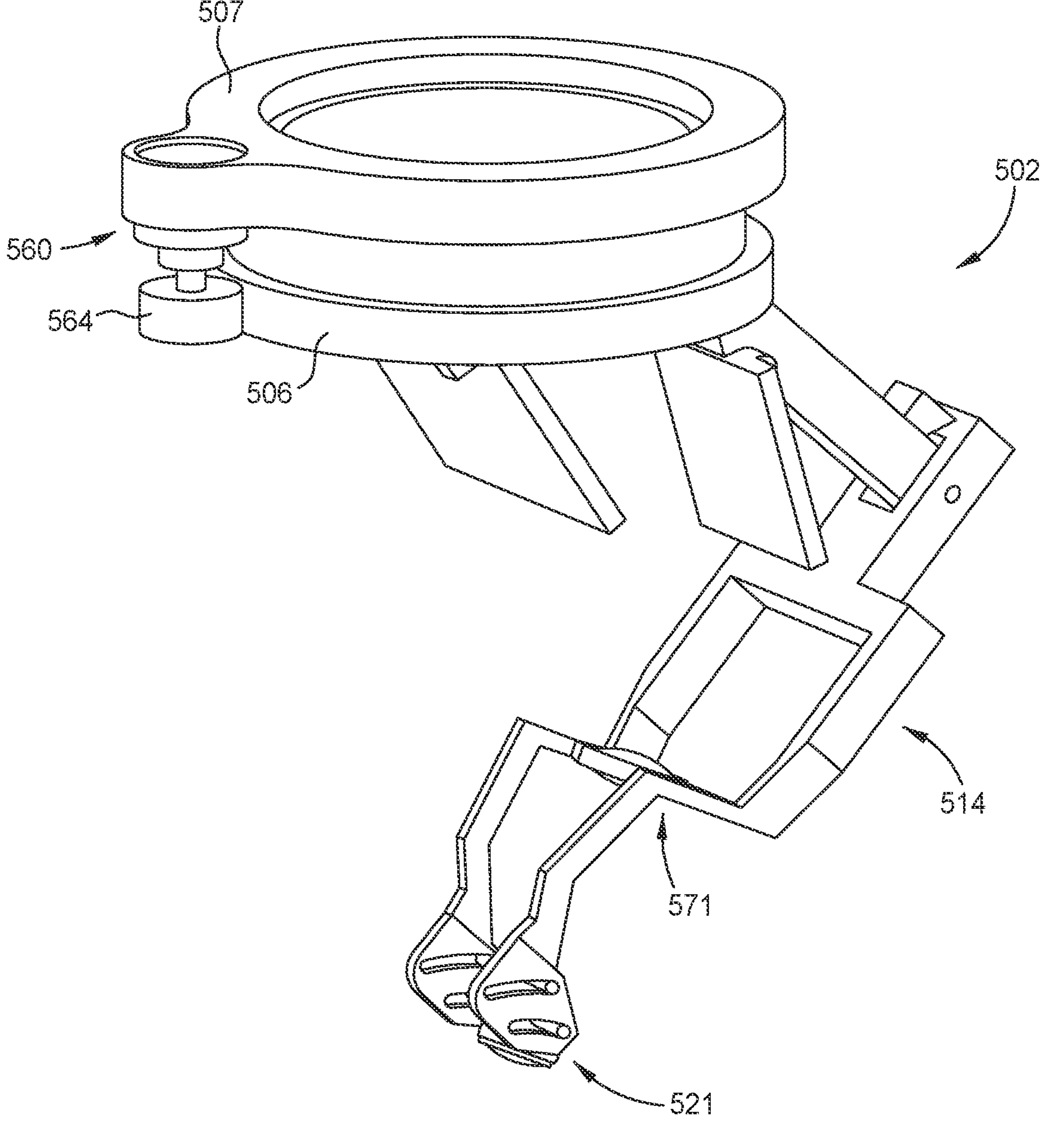
FIG. 5 shows an ophthalmic viewing device having a motorized rotation feature, according to certain embodiments.

FIG. 5 shows an ophthalmic viewing device 502 having another exemplary motorized rotation feature 560, according to certain embodiments. As shown, the ophthalmic viewing device 502 is similar to the ophthalmic viewing device 302 of FIGS. 3A-B, however, with a motorized rotation feature 560 having a vertical orientation. In the embodiments of FIG. 5, the motorized rotation feature 560 includes a spinner 564 that is set into a housing in a stationary mounting ring 507 and engages a rotatable ring 506. The spinner 564 is operated by a motor that may be housed within a visualization device (e.g., visualization device 105) that couples to the stationary mounting ring 507. In embodiments where the visualization device is digital, the motor may be powered by the visualization device's power system. For example, a digital visualization device may have at least three motors with corresponding motor drivers that may be used to motorize the rotation feature 560. In the embodiments of FIG. 5, the spinner 564 engages the rotating ring 506 on an outer portion of the rotating ring 506. In some embodiments, instead of the motor being housed within a visualization device, the motor can be mounted outside the visualization device and attached to the stationary ring 507 to engage the rotating ring 506. In some embodiments, such as for use with an analog visualization device, a separate power source and driver may be provided to drive the motor for operating the spinner 564.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ophthalmic viewing device ("viewing device"), comprising:

a mounting feature configured for mounting the viewing device to a visualization device;

an upper arm connected to the mounting feature proximate a proximate end of the upper arm;

a lower arm connected to the upper arm proximate a distal end of the upper arm;

a first mirror movably connected to the mounting feature and having at least a first mirror position and a second mirror position;

a second mirror connected to the upper arm; and a lens assembly having a lens frame configured to shift between a first lens frame position and a second lens frame position, the lens frame having a central cavity configured for receiving a lens, wherein:

in a first configuration of the viewing device:

the lens frame is in the first lens frame position, such that a plane of the central cavity is perpendicular to an axis of the visualization device ("visualization device axis") along an on-axis optical path between a patient's eye and the visualization device for viewing a first field of view of the patient's eye, the on-axis optical path comprising a first path traversed by light reflected from the patient's eye to the visualization device; and the first mirror is in the first mirror position outside of the on-axis optical path; and in a second configuration of the viewing device:

the lens frame is in the second lens frame position, wherein in the second lens frame position the plane of the central cavity is disposed at a frame angle relative to the visualization device axis, such that the plane of the central cavity is perpendicular to a first angled axis of an off-axis optical path, the off-axis optical path comprising a second path traversed by the light reflected from the patient's eye to the visualization device;

the first mirror is in the second mirror position, wherein in the second mirror position, the first mirror:

at least partially intercepts the on-axis optical path, and is positioned at a first angle relative to the visualization device axis for redirecting the off-axis optical path, received along a second angled axis from the second mirror, towards the visualization device; and the second mirror is:

positioned within the off-axis optical path at a second angle relative to the visualization device axis, and configured to redirect the light reflected from the patient's eye along the off-axis optical path, received along the first angled axis from the lens in the lens frame in the second lens frame position, towards the first mirror for viewing a second field of view of the patient's eye that is different from the first field of view.

2. The viewing device of claim 1, wherein:

the lower arm comprises two extensions, the lower arm comprises two pairs of slots at corresponding distal ends of the two extensions, the lens frame comprises two pairs of pins, including one pair of pins on one side of the lens frame and another pair of pins on another side of the lens frame.

3. The viewing device of claim 2, wherein the two pairs of pins are configured to engage with the corresponding two pairs of slots to enable shifting the lens frame from the first lens frame position to the second lens frame positions and vice versa.

4. The viewing device of claim 1, wherein the lower arm comprises a second lens frame configured for receiving a second lens.

5. The viewing device of claim 4, wherein a second plane of the second lens frame is disposed at a second frame angle relative to the visualization device axis, the second frame angle being parallel to the frame angle of the central cavity of the lens frame when the lens frame is in the second lens frame position.

6. The viewing device of claim 1, wherein the lower arm is removably connected to the upper arm.

7. The viewing device of claim 1, wherein the lens frame is configured to shift into more than two lens frame positions.

8. The viewing device of claim 1, wherein the mounting feature comprises:

a stationary ring removably mounted to the visualization device; and a rotatable ring attached to and rotatable with respect to the stationary ring, wherein the upper arm is connected to the rotatable ring.

9. The viewing device of claim 8, further comprising a motorized rotation feature coupled to the rotatable ring of the mounting feature, the motorized rotation feature being configured to rotate the rotatable ring.

10. The viewing device of claim 9, wherein the motorized rotation feature comprises a spinner that is set into the stationary ring and that engages the rotatable ring.

11. The viewing device of claim 9, wherein the motorized rotation feature is controlled by a foot-activated pedal or a remote.

12. The viewing device of claim 1, wherein the lens is aspheric.

13. The viewing device of claim 1, wherein the upper arm and the lower arm are connected at a hinged connection-location, and the upper arm includes a stop proximate the hinged connection-location and configured to restrict motion of the lower arm.

14. The viewing device of claim 1, further comprising a primary switch, the primary switch being configured to simultaneously move the first mirror between the first mirror position and the second mirror position and the lens frame between the first lens frame position and the second lens frame position.

15. The viewing device of claim 1, wherein the first angle is between 15 degrees and 75 degrees.

16. The viewing device of claim 1, wherein the frame angle is between 15 degrees and 25 degrees.

17. The viewing device of claim 1, wherein the second angle is between 15 degrees and 75 degrees.

* * * * *